US009384325B2

(12) United States Patent
Ramamurthi et al.

(10) Patent No.: US 9,384,325 B2
(45) Date of Patent: *Jul. 5, 2016

(54) SYSTEM AND METHOD FOR GENERATING ENHANCED DENSITY DISTRIBUTION IN A THREE DIMENSIONAL MODEL OF A STRUCTURE FOR USE IN SKELETAL ASSESSMENT USING A LIMITED NUMBER OF TWO DIMENSIONAL VIEWS (71) Applicant: Hologic, Inc., Bedford, MA (US)

(72) Inventors: Krishna Ramamurthi, Somerville, MA (US); Kevin Wilson, Acton, MA (US)

(73) Assignee: Hologic Inc, Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/246,281

(22) Filed: Apr. 7, 2014

(65) Prior Publication Data
US 2014/0222391 A1    Aug. 7, 2014

Related U.S. Application Data (63) Continuation of application No. 12/727,496, filed on Mar. 19, 2010, now Pat. No. 8,693,634.

(51) Int. Cl.
*A61B 6/03* (2006.01)
*G06F 19/00* (2011.01)
(Continued)

(52) U.S. Cl.
CPC ............ *G06F 19/3437* (2013.01); *A61B 6/505* (2013.01); *A61B 6/5247* (2013.01); *G06T 11/006* (2013.01); *G06T 19/20* (2013.01); *G06T 2210/41* (2013.01); *G06T 2211/436* (2013.01)

(58) Field of Classification Search
CPC ....................................................... A61B 6/505

USPC ........... 378/4, 5, 16, 65, 98.9, 98.11, 901, 62; 382/128, 131; 600/425, 427
See application file for complete search history.

(56) References Cited

U.S. PATENT DOCUMENTS 5,251,128 A * 10/1993 Crawford ............... A61B 5/113
                                                    600/425
5,852,646 A * 12/1998 Klotz et al. ...................... 378/8
(Continued)

FOREIGN PATENT DOCUMENTS

| GB | 2250164 A | 5/1992 |
| WO | WO2007058918 A2 | 5/2007 |
| WO | WO2008078259 A2 | 3/2008 |

OTHER PUBLICATIONS

Yao, Tetrahedral Mesh Modeling of Density Data for Anatomical Atlases and Intensity-based REgistration, MICCAI 2000, LNCS 1935, pp. 531-540.
(Continued)

*Primary Examiner* — Allen C. Ho (57) ABSTRACT

A method of generating a density enhanced model of an object is described. The method includes generating a customized a model of an object using a pre-defined set of models in combination with at least one projection image of the object, where the customized model is formed of a plurality of volume elements including density information. A density map is generated by relating a synthesized projection image of the customized model to an actual projection image of the object.ABS Gains from the density map are back-projected into the customized model to provide a density enhanced customized model of the object. Because the density map is calculated using information from the synthesized projection image in combination with actual projection images of the structure, it has been shown to provide spatial geometry and volumetric density results comparable to those of QCT but with reduced patient exposure, equipment cost and examination time.

11 Claims, 6 Drawing Sheets

(51) Int. Cl.
*A61B 6/00* (2006.01)
*G06T 19/20* (2011.01)
*G06T 11/00* (2006.01)

(56) References Cited

U.S. PATENT DOCUMENTS

| | | | |
|---|---|---|---|
| 5,901,199 A | 5/1999 | Murphy | |
| 6,125,164 A | 9/2000 | Murphy | |
| 6,144,759 A | 11/2000 | Weese | |
| 6,470,207 B1 | 10/2002 | Simon | |
| 6,516,046 B1 | 2/2003 | Frohlick | |
| 6,549,645 B1 | 4/2003 | Oikawa | |
| 6,711,432 B1 | 3/2004 | Krause | |
| 6,744,848 B2 * | 6/2004 | Stanton et al. | 378/55 |
| 6,816,564 B2 * | 11/2004 | Charles, Jr. | A61B 6/032 378/18 |
| 6,823,044 B2 | 11/2004 | Rosner | |
| 6,865,253 B2 | 3/2005 | Blumhofer | |
| 6,959,067 B2 * | 10/2005 | Rasche et al. | 378/8 |
| 7,010,080 B2 | 3/2006 | Mitschke | |
| 7,103,139 B2 | 9/2006 | Nagaoka | |
| 7,167,738 B2 * | 1/2007 | Schweikard et al. | 600/407 |
| 7,180,976 B2 * | 2/2007 | Wink et al. | 378/8 |
| 7,187,792 B2 | 3/2007 | Fu | |
| 7,204,640 B2 | 4/2007 | Fu | |
| 7,453,984 B2 * | 11/2008 | Chen | A61N 5/1049 378/65 |
| 7,522,779 B2 * | 4/2009 | Fu et al. | 382/254 |
| 7,545,907 B2 * | 6/2009 | Stewart | A61B 6/02 378/108 |
| 7,734,009 B2 * | 6/2010 | Brunner et al. | 378/62 |
| 7,806,589 B2 * | 10/2010 | Tashman et al. | 378/197 |
| 7,881,424 B2 * | 2/2011 | Zhang | G01T 1/1648 378/5 |
| 7,894,649 B2 * | 2/2011 | Fu | A61N 5/1049 378/65 |
| 8,005,284 B2 * | 8/2011 | Sakaguchi et al. | 382/131 |
| 8,206,153 B2 * | 6/2012 | Suttin | A61C 8/00 433/215 |
| 8,295,435 B2 | 10/2012 | Wang | |
| 8,295,570 B2 * | 10/2012 | Markwardt et al. | 382/128 |
| 8,300,911 B1 * | 10/2012 | Payne et al. | 382/128 |
| 8,345,821 B2 | 1/2013 | Sumanaweera | |
| 8,634,629 B2 * | 1/2014 | Wilson | 382/132 |
| 8,693,634 B2 * | 4/2014 | Ramamurthi | A61B 6/505 378/62 |
| 8,725,231 B2 * | 5/2014 | Nicolella | A61B 5/103 600/407 |
| 8,885,910 B2 * | 11/2014 | Edic | G06T 11/003 378/166 |
| 8,923,592 B2 * | 12/2014 | Wollenweber et al. | 382/131 |
| 2003/0223537 A1 | 12/2003 | Puzas | |
| 2004/0167390 A1 | 8/2004 | Alexander et al. | |
| 2004/0242987 A1 | 12/2004 | Liew | |
| 2006/0062442 A1 | 3/2006 | Arnaud | |
| 2009/0091567 A1 | 4/2009 | Fu | |

OTHER PUBLICATIONS

Yao, Construction and Simplification of Bone Density Models, Medical Imaging 2001: Image Processing, Proceedings of SPIE vol. 4322 (2011) pp. 814-834.
Jul. 16, 2015 European Search Report for app No. 11757051.5.

* cited by examiner

SYSTEM AND METHOD FOR GENERATING ENHANCED DENSITY DISTRIBUTION IN A THREE DIMENSIONAL MODEL OF A STRUCTURE FOR USE IN SKELETAL ASSESSMENT USING A LIMITED NUMBER OF TWO DIMENSIONAL VIEWS

CROSS-REFERENCE TO RELATED APPLICATION

This application is a continuation application of U.S. patent application Ser. No. 12/727,496, filed Mar. 19, 2010, now U.S. Pat. No. 8,693,634, issued on Apr. 8, 2014, which is incorporated by reference herein.

FIELD OF THE INVENTION

The present invention relates generally to the field of skeletal assessment and more particularly to a system and method for generating enhanced density distributions in a 3-D model of a structure for use in skeletal assessment.

BACKGROUND OF THE INVENTION

Currently 2-D Dual-energy X-ray Absorptiometry is the gold standard of osteoporosis assessment. Dual-energy X-ray absorptiometry (DXA) is a means of performing skeletal assessment using x-ray beams of differing energy levels. A DXA system generally includes an examination table and a C-arm at opposite ends of which are mounted an x-ray tube and a multi-detector array. The patient is positioned on the examination table between the x-ray tube and the detector array of the C-arm and a fan-shaped beam of x-rays are directed from the tube to the detector as the tube and detector are scanned axially along the patient. The X-rays are alternatively pulsed at high and low energy ranges. By comparing the relative attenuation of the x-rays at the two energies, the contributions to the attenuation due to the soft tissue can be subtracted. When soft tissue absorption is subtracted out, a two dimensional image of the bony structure of the patient remains and may be used for skeletal assessment purposes.

DXA has grown to be the gold standard for osteoporosis assessment because it provides improved skeletal assessment results (in comparison to single energy x-rays) while minimizing patient exposure to radiation. However one problem with DXA is that it fails to provide important 3-D information about the volumetric density and spatial geometry of imaged skeletal structures. Such 3-D information may be obtained using Quantitative Computed Tomography (QCT) Densitometry. The QCT examination is performed using a CT scanner to obtain volumetric data. One issue with QCT lies in whether the quality of the information obtained by 3D structural evaluation using QCT outweighs the patient's increased exposure to radiation, the financial costs associated with QCT and the clinical feasibility of actual QCT practice.

Attempts have been made to leverage the information provided by DXA to obtain skeletal assessment information of similar quality to that provided by QCT. These attempts have involved selecting a standard 3-D model of a skeletal structure of a patient from an atlas of structures, and customizing the 3-D model by varying its modes of deformation until digitally reconstructed radiographs (DRRs) (i.e., 2-D projection images) of the 3-D model can be 'matched' to co-registered DXA projection images of the patient. With such an arrangement a customized 3-D VXA model of a skeletal structure may be obtained using only a handful of DXA projection images, thereby minimizing patient exposure while theoretically providing improved quality skeletal assessment data.

However it has been determined that not all of the skeletal health assessment information provided by a customized VXA model meets the quality standards of QCT. Customized VXA models have shown great accuracy for skeletal assessment measurements related to the spatial geometry of the structure. However, measurements which attempt to quantify the volumetric density of the skeletal structure, and in particular the Bone Mineral Density (BMD), have proven less reliable. It would be desirable to identify a method for obtaining volumetric density information having accuracy comparable to that provided by QCT yet at DXA dosing levels.

SUMMARY OF THE INVENTION

According to one aspect of the invention, a method of generating a density enhanced model of an object includes the steps of generating a customized model of an object using a pre-defined set of models in combination with at least one projection image of the object, the customized model comprising a plurality of volume elements including density information. A density map is generated by relating a synthesized projection image of the customized model to a projection image of the object. Gains from the density map may be back-projected into the customized model to provide a density enhanced customized model of the object. The density enhanced customized model may then be stored for later use in skeletal assessment and/or displayed at a user interface. Because the density map is calculated using information from the synthesized projection image in combination with actual projection images of the structure, it has been shown to provide spatial geometry and volumetric density results comparable to those of QCT but with reduced patient exposure, equipment cost and examination time.

According to another aspect of the invention, a system for assessing density characteristics of an object includes a processor, a storage medium for storing a projection image of an object and program code stored in the storage medium. The program code is operable when executed upon by the processor to: generate a customized a model of the object using a generic model of the object and the projection image of the object, the customized model comprising a plurality of volume elements, each volume element including density information, generate a density map using a synthesized projection image of the customized model and a projection image of the object and back-project gains from the density map into the customized model to modify the density information of each of the volume elements to provide a density enhanced customized model of the object and thereby transform the generic model of the object into an object specific model; and wherein the density enhanced customized model of the object is stored in the storage medium.

According to a further aspect of the invention, a density map is stored in a computer readable memory of a processing system. The density map comprises an M×N array of density elements derived from an M×N projection image of an object and an M×N synthesized projection image of a generic three dimensional model which has been customized using the projection image of the object. The density map is constructed by comparing the image of the object with the synthesized projection image of the three dimensional model. The density map thus constructed is used to transform the customized, generic three dimensional model into an object specific three dimensional model.

DETAILED DESCRIPTION

According to one aspect of the invention it is realized that a customized three-dimensional model of an imaged structure may be further transformed by applying one or more different gains to volume elements of the model to provide a density enhanced 3-D model of the imaged structure. Such a density-enhanced 3-D model of the image structure has been found to have spatial geometry and volumetric density information similar in quality to a QCT representation of the imaged structure. The gains that are applied to the volume elements of the 3-D model are determined by relating density information from projection images of the customized 3-D model to density information from one or more DXA images of the imaged structure. The present invention therefore provides improved skeletal assessment using 2-D images, thereby reducing patient exposure, procedure complexity and equipment cost.

Figure 1:
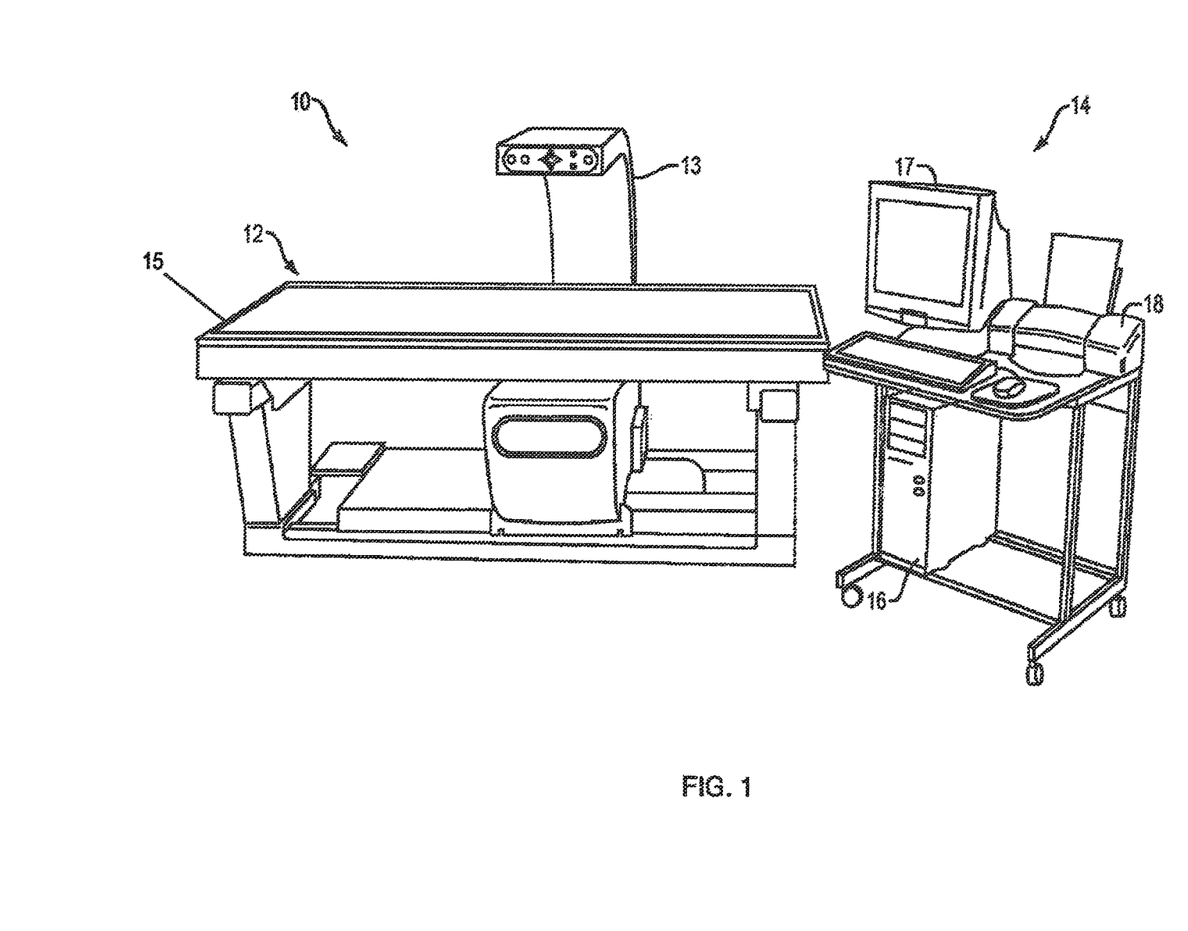
FIG. 1 is illustrates an exemplary skeletal assessment environment in which the present invention may be used to generate, store and/or display density enhanced volume dual-energy x-ray absorptiometry (E-VXA) models.

Skeletal assessment using models of the present invention may be performed in a variety of environments using one or more two-dimensional images obtained from any one of a variety of imaging devices. By way of example and not limitation, FIG. 1 illustrates a representative one of the skeletal assessment environments 10 including an imaging device 12 for capturing one or more two-dimensional images and a workstation 14, including a processing tower 16 and output devices/displays such as display 17 and printer 18. The imaging device 12 of FIG. 1 may be, for example, an osteodensitometer such as the Discovery™-A QDR Bone Densitometer, provided by Hologic, Inc. of Bedford Ma. The imaging device 12 includes a C-arm 13 with a fan beam x-ray source on one arm and an x-ray detector array on an opposing arm. During image capture, a patient is positioned on the examination table 15 between the x-ray source and the x-ray detector array of the C-arm 13 and a fan-shaped beam of x-rays are directed from the x-ray source to the x-ray detector array as the x-ray source and x-ray detector array are scanned axially along the patient. The X-rays are alternatively pulsed at high and low energy ranges and one or more images are captured and processed to provide Dual X-ray Absorptiometry (DXA) projection images.

It should be noted that although the specification describes a method of constructing a density enhanced VXA model using one or more DXA images, the present invention is not limited to use with DXA images. DXA images are discussed because at present they are preferred for osteoporosis assessment. However it will be appreciated that the methods described herein may be used with any 2-D projection images of a structure, whether it be DXA, x-ray etc. In addition it should be noted that it is not required that the 2-D images be obtained immediately prior to skeletal assessment; rather the present invention may be used to provide improved skeletal assessment for images previously captured and stored, for images captured on film and digitized, etc.

Figure 2:
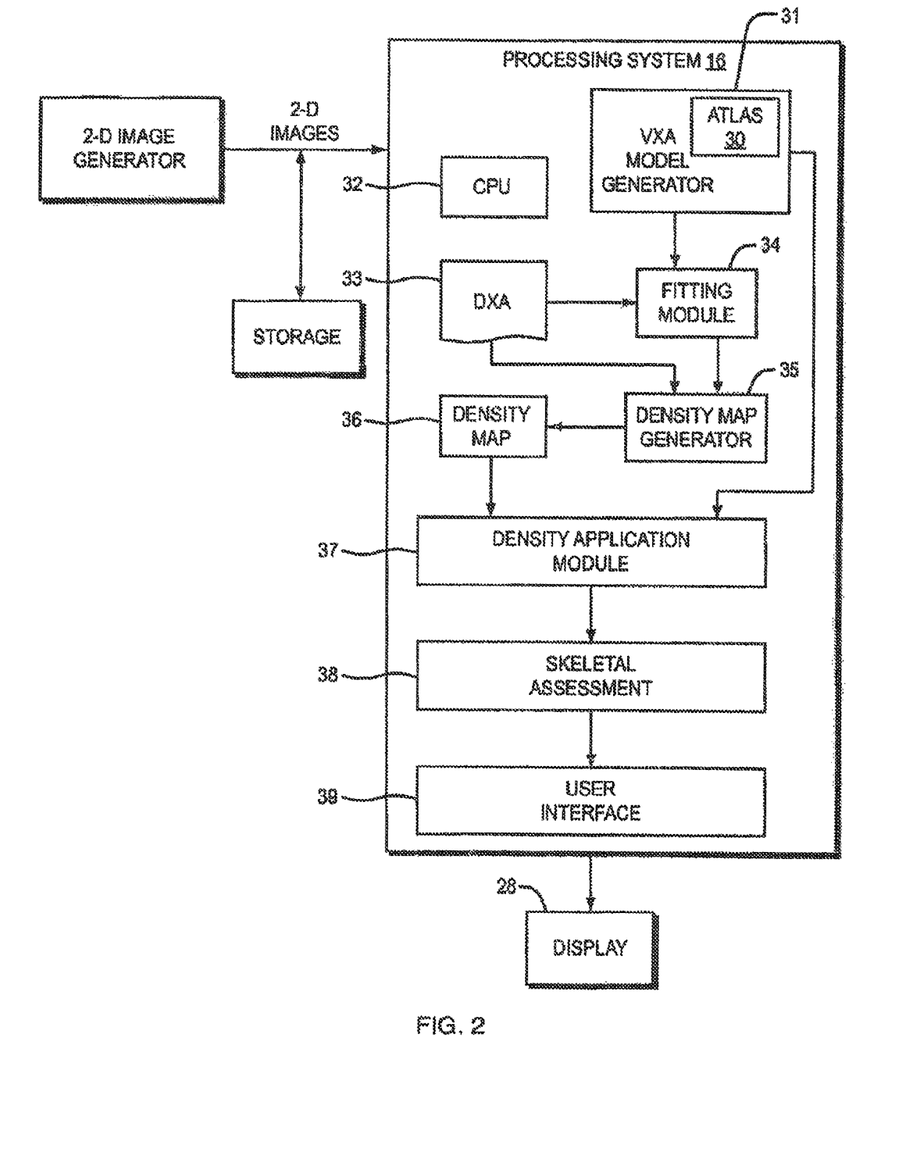
FIG. 2 is a block diagram illustrating several components of the system of FIG. 1 which support the present invention.

The imaging device 12 is coupled via a network to the workstation 14. The workstation 14 includes software for controlling the scan operation of imaging device 12 as well as for processing and analyzing the DXA projection images. FIG. 2 illustrates functional components of the processing tower 16 in more detail. In general the processing tower 16 includes one or more central processors, functional modules and data structures 31-39. The functional modules may be comprised of hardware, software or any combination thereof, while the data structures may be stored in a local or remote memory. Any software modules are operable, when executed upon by the processors, to perform specific pre-defined functions. For the purposes of clarity FIG. 2 illustrates the software programs as discrete functional modules resident in memory blocks on the processing tower 16 although it is readily appreciated by those of skill in the art that software programs may be combined along different functional boundaries and may reside in any storage accessible to the processors, whether it is on the processing tower 16 itself or located remotely. Accordingly the present invention is not limited to embodiments delineated as shown in FIG. 2.

Representative components of a processing tower 16 system of FIG. 2 that may be used in or by the present invention include a VXA model generator 31 including an atlas 30, DXA projection images 33 and a Fitting module 34. As will be described in more detail with regard to FIGS. 3 and 4, the Fitting module 34 performs an iterative process whereby a model from the VXA model generator 31 is deformed and compared to the DXA projection images until a 'best fit match' is found between the model and the DXA projection images. The resulting, 'custom' 3D VXA model is then forwarded to density map generator 35. As will be described in more detail with regard to FIG. 4, the density map generator 35 uses information from the custom 3D VXA model together with information from the DXA projection images to generate a density map 36. The density map 36 is forwarded together with the custom 3D VXA model to a density application module 37 which applies the gains from the density map 36 to the custom 3D VXA model to provide a density-enhanced 3D VXA model. The density-enhanced 3D VXA model may then be forwarded to the skeletal assessment module 38, and results of skeletal assessment may be output via a user interface 39 to one or more displays 28 or other output devices.

Figure 3:
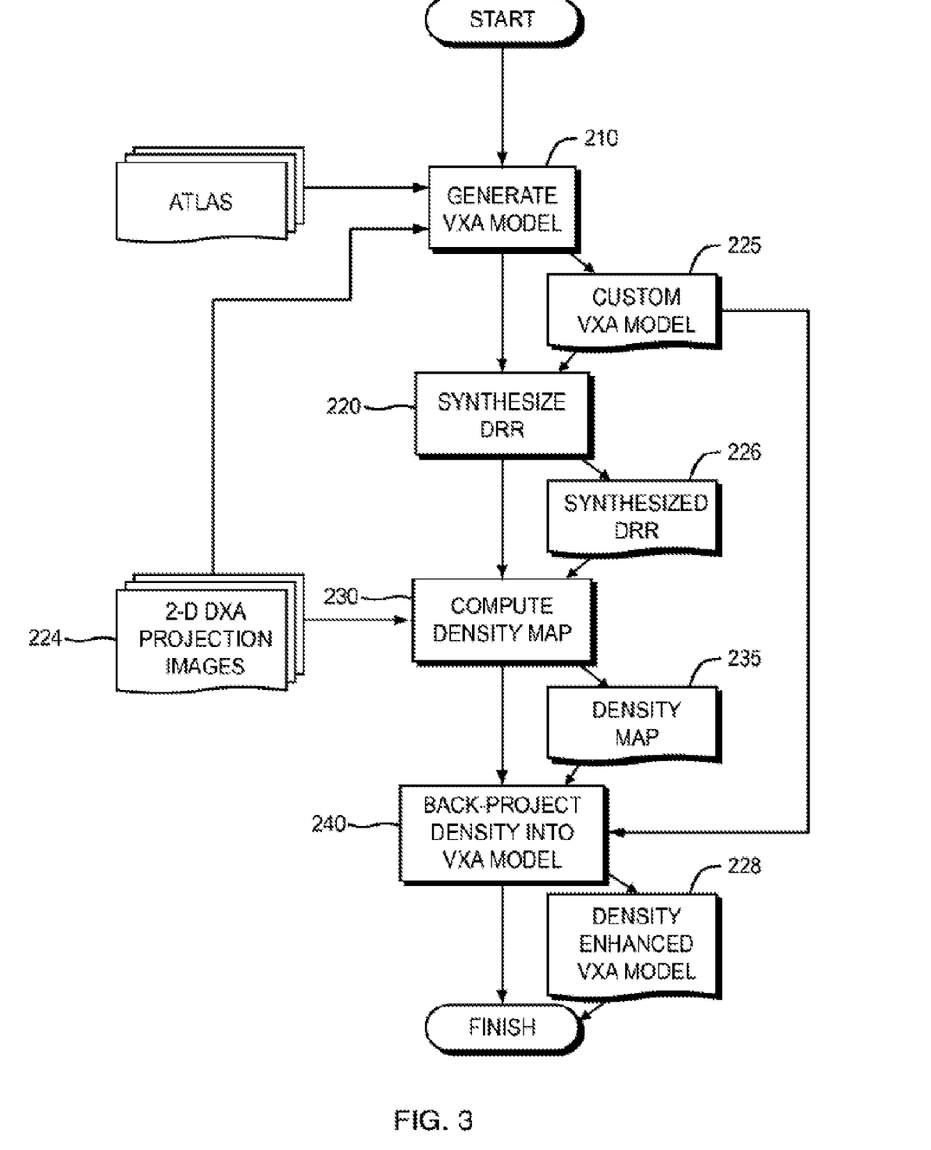
FIG. 3 is a flow diagram illustrating exemplary steps that may be performed to generate the density enhanced VXA model of the present invention.

FIG. 3 is a flow diagram provided to describe, in more detail, exemplary steps that may be performed in the generation of a density enhanced VXA model of the present invention. As mentioned previously, DXA projection data alone fails to provide important 3-D information about the volumetric density and spatial geometry of imaged skeletal structures. Efforts have therefore been made to generate a three dimensional volumetric dual energy x-ray absorptiometry (VXA) model using the limited number of DXA projection images. One technique involves generating a VXA model using a deformable density atlas. The atlas is a statistical data set that is constructed from a large set of Computed Tomography (CT) scans which mathematically embodies an a priori shape of a structure. The statistical atlas includes one or more models of segmented CT data, wherein each model may have one or more different modes of deformation defining anatomical differences of the structure. For example using a large number of femurs (i.e. fifty or more) a specific tetrahedral mesh model of the femur is formed by mathematically fitting the femur data to a tetrahedral mesh model by deforming the average femur mesh to fit each feature of the femur. Normal, orthogonal modes of variation for the model may then be identified using Principal Component Analysis (PCA) or robust PCA techniques known to those of skill in the art. Thus the atlas comprises a set of deformable models of bone structures, each model having defined modes of deformation which are typically orthogonal such that modification of one mode does not affect the other deformation modes.

As known in the art of 3-D modeling, a 3-D model is generally represented by a set of volume elements, each volume element defining a three dimensional structure having one or more attributes defining characteristics of the volume element including spatial attributes and composition attributes. For example, spatial attributes may include information as to the location of the volume element within the 3-D structure, while composition attributes may provide information such as the intensity of pixels in the volume element, where the intensity relates to the density of the structure. The shape of the three dimensional structure of a volume elements is a matter of design choice, and includes but is not limited to rectilinear 'voxels' or tetrahedral 'tetras'. It is noted that the various forms of volume rendering each have their own advantages. For example, *Tetrahedral Mesh Modeling of Density Data for Anatomical Atlases and Intensity-Based Registration*, by Yao and Taylor, in MICCAI 2000, 2000. Pittsburgh Pa., USA, Springer and *Construction and Simplification of Bone Density Models*, by Yao and Taylor, Proceedings of SPIE Vo. 4322 (2001) pp. 814-823 (both incorporated herein by reference) disclose construction of a hierarchical tetrahedral mesh model for use in a bone density atlas for at least the reason that tetrahedral meshes can be stored more efficiently than voxelized representations. Thus the 3-D model may be represented in terms a voxel or as a tetrahedral mesh. Converting between tetrahedral models and voxelized models may readily be accomplished by those of skill in the art.

Figure 4:
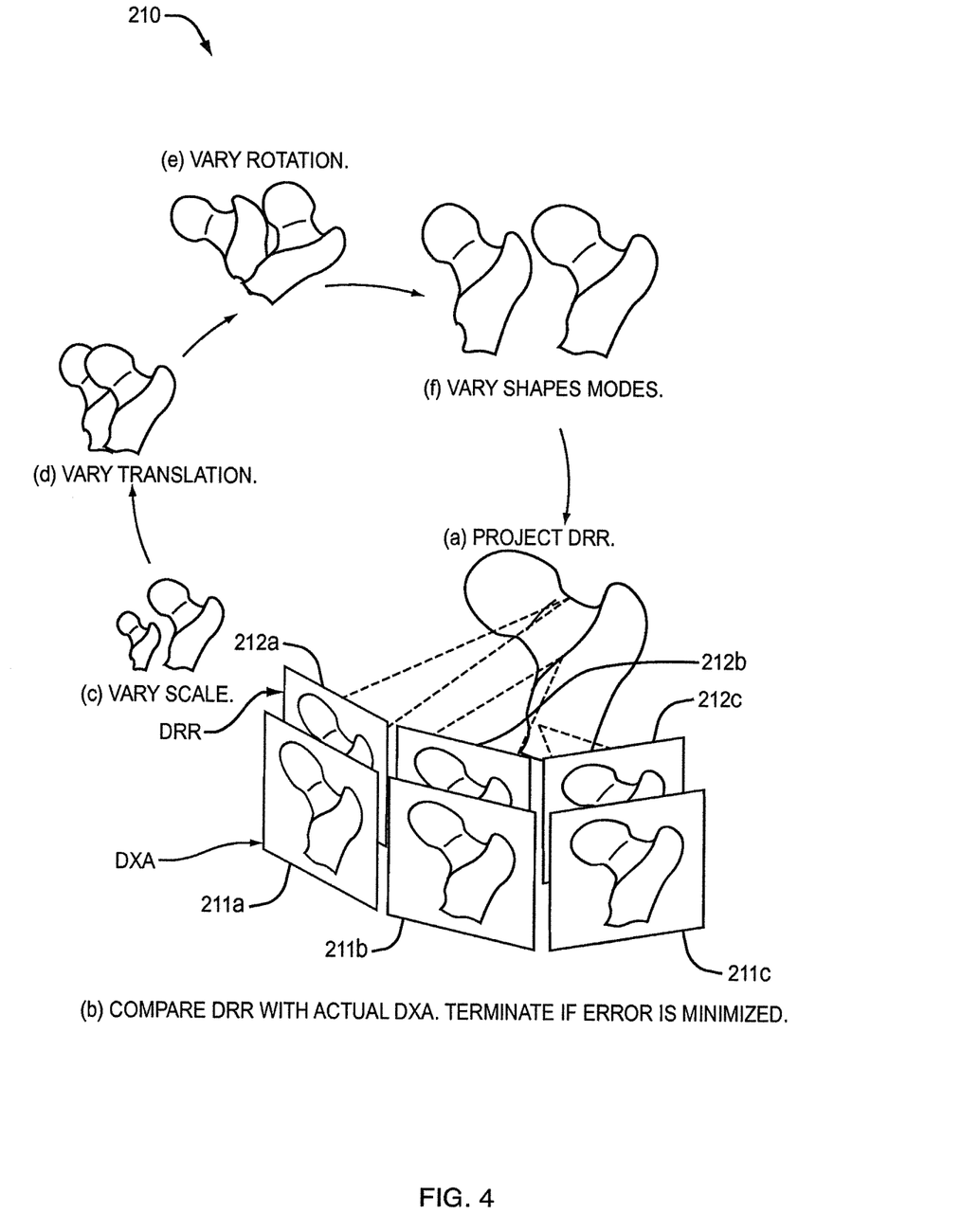
FIG. 4 is a functional flow diagram provided to illustrate a method for generating a customized VXA model for use with the present invention.

The initial step 210 of the process of FIG. 3 involves generating a 'customized VXA model' by deforming a generic 3-D model using information from a limited number (for example 4 or less) of 2D DXA projection images 224. FIG. 4 illustrates the process of step 210 (also described in the Yao reference) in more detail. At step 210(*a*) one or more Digitally Reconstructed Radiographs (DRR) are synthesized and compared to associated 2D DXA projection images. Synthesizing DRR images involves transforming between a coordinate system associated with the 3D model and the 2D coordinate system of the 2D DXA projection images. For example, the coordinate system of the 2D DXA projection images may be defined in terms of projection geometry parameters, including image center, pixel size, camera focal length, projection angle, etc. A variety of techniques known to those of skill in the art may be used to generate 2D DRR images of the 3D model that are registered to coordinate system of the 2D DXA projection images and the present invention is not limited to any particular method of projection. The resulting DRR is a 2D image matched in image and pixel size to the 2D DXA projection image. FIG. 4 illustrates 3 2D DXA projection images (211*a*, 211*b* and 211*c*), and 3 co-registered DRRs (212*a*, 212*b* and 212*c*).

At step 210(*b*) a comparison is performed between each of the projected DRRs and the corresponding 2D DXA projection images to determine whether the 3D model 'matches' the imaged structure associated with the 2D DXA projection images. A variety of methods of determining when there is a 'best fit match' between the imaged structure and the 3D VXA model can be used. For example, a pixel-by-pixel comparison of the images may be performed to identify differences in pixel intensity value, and a model may be determined to be a best fit match if the differences in pixel intensity value for the image(s) are below a pre-identified threshold. Other methods, such as the as simulated annealing and amoeba methods of minimization known to those of skill in the art are also within the scope of the present invention. Should the 3D VXA model which generated the DRR images fail to be a 'best fit match' to the images structure any one of steps 210(*c*), 210(*d*) or 210(*e*) may be executed to transform (by varying the rotation, translation or scale) of the 3D VXA model. Alternatively, or in conjunction with any of the steps 210(*c*), 210(*d*) or 210(*e*), one or more modes of the 3D VXA model may be modified at step 210(*f*). The process of transforming and deforming the model, and generating DRRs and comparing the DRRs to the 2D DXA projection images continues until the differences between the DRR images and 2D DXA projection images are within 'best fit match' threshold. Once the best fit match has been determined, the transformed and/or deformed 3D VXA model is stored as a 'custom VXA' 225 model. It should be noted that the above process is merely an exemplary method for customizing a 3D VXA model of an imaged structure. It is appreciated that other methods of customizing a 3D VXA model, for example that do not depend upon an atlas but use other means, are known and implemented by those in the volume rendering art. Therefore, although an exemplary method of generating a custom 3D VXA model has been shown and described, the present invention is not limited to the described process.

Referring back to FIG. 3, as discussed above the custom 3D VXA model generated using the process of step 210 has been found to lack accuracy in its representation of the internal structure (i.e. density) of the imaged structure. According to one aspect of the invention it is realized that improved density representation may be obtained by applying gains across the 3D VXA model, where the gains are represented in a density map that associates pixel intensity values of the 2D DXA projection images with the pixel intensity values of the DRRs of the custom 3D VXA model according to the below Equation I.

$$G_{(M,N)} = DXA\_PI_{(M,N)} / DRR_{(M,N)} \qquad \text{Equation I}$$

Wherein the DXA projection image, DRR synthesized image and Density Map comprise an M×N array of elements, and wherein DXA_PI(M,N) is the pixel intensity value of the 2D DXA projection image at location (M,N) of the 2D DXA projection image, and DRR(M,N) is the pixel intensity value of the DRR at location (M,N) of the DRR.

Figure 5:
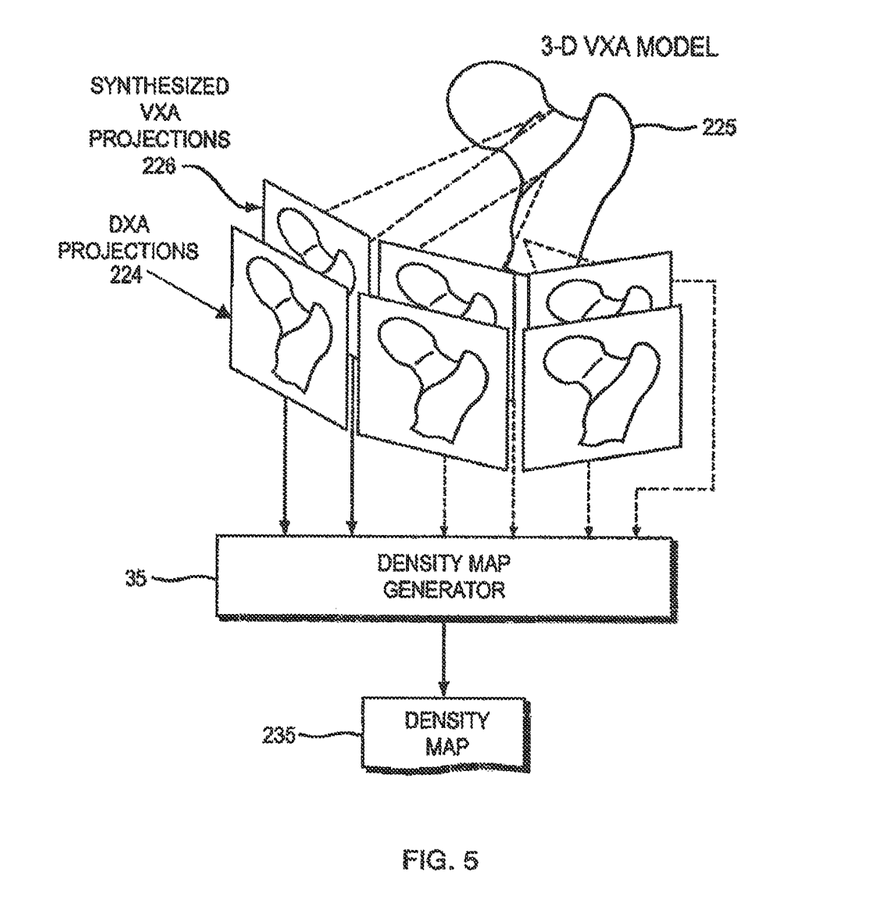
FIG. 5 is a diagram illustrating how images may be used to generate a density map of the present invention.

At step 220 at least one DRR 226 is synthesized from the customized VXA model 225 and at step 230 at least one 2D DXA projection image 224 is compared to the synthesized DRR 226 to generate density map 235. FIG. 5 is a pictorial representation of steps 220 and 230. Although FIG. 5 illustrates that multiple DRR images and 2D DXA projection images are used for density map generation, it should be appreciated that, although possible, it is not necessary to employ more than a single DXA/DRR image pair for density map generation and therefore only one DXA/DRR image pair is shown with solid lines (rather than dashed) as input to the density map generator 35. However alternate embodiments where multiple density maps are initially generated and combined, for example by averaging the resulting gains, or by selecting a maximum or minimum gain, or some combination thereof, are also within the scope of the present invention.

Figure 6:
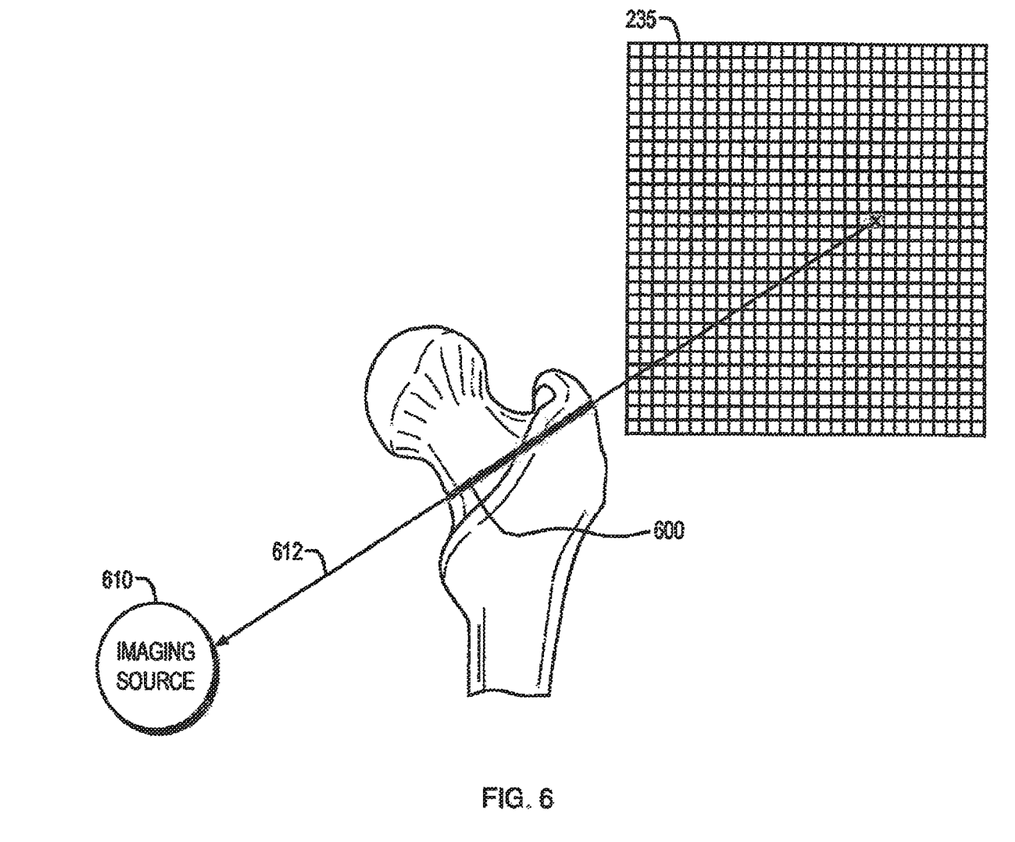
FIG. 6 is a diagram intended to illustrate back-projection of density from the density map into the customized VXA model to generate the density enhanced VXA model of the present invention.

Once the density map is generated, at step 240 it is back projected into the custom VXA model 225 to generate a density enhanced custom VXA model 228. Back-projection involves identifying all of the voxels in the 3-D structure that contribute to an intensity value of a particular 2-D projected pixel, and applying the computed density for that pixel to each of the voxels. For example, referring now to FIG. 6 the density map 235 was generated from a DRR and D×A image having a particular projection angle relative to the imaging source 610 indicated by line 612; that the x-rays from the imaging source 610 that follow the trajectory of line 612 will impact the value of the pixel X in density map 235. In the 3-D tetrahedral mesh model, the x-ray traverses multiple tetra (or voxels) in its path through the model. During back-projection, the calculated density value from pixel x is applied to all of the volume elements along the path (indicated by line 600). Regardless of how the density of the 3-D model is represented (i.e., as a discrete value or as a density function), the density is multiplied to the density representation.

Because the density is calculated using patient specific DXA projection information, the resulting density enhanced 3D VXA model includes patient specific density information. As a result the model is capable of being used to obtain skeletal assessment information that is comparable to that QCT, but which uses a limited number of x-ray views and therefore reduces patient exposure and procedure cost.

Accordingly a method and system for generating a density enhanced 3D model for use in skeletal assessment has been shown and described. Having described exemplary embodiments, it can be appreciated that the examples described above are only illustrative and that other examples also are encompassed within the scope of the appended claims.

What is claimed is:

1. A computer implemented method of generating a density enhanced customized model of an object comprising:
    generating a customized model of an object using a generic model of the object, the customized model comprising at least one volume element, the at least one volume element including density information;
    generating a density map using a synthesized projection image of the customized model and a projection image of the object;
    modifying the density information of the at least one volume element with information from the density map into the customized model to provide a density enhanced customized model of the object; and
    performing at least one of storing the density enhanced customized model of the object and displaying the density enhanced customized model of the object on a user display.

2. The method of claim 1, wherein modifying the density information of the at least one volume element with information from the density map into the customized model comprises back-projecting gains from the density map into the customized model.

3. The method of claim 1, wherein the object comprises a bone, the density information is associated with a density of the bone.

4. The method of claim 3, wherein the method further comprises determining a bone mass density (BMD) of the object using the density enhanced customized model of the object.

5. The method according to claim 1, wherein generating a customized model of the object comprises:
    selecting a standard model of a structure of a same type as the object, from a set of pre-defined three-dimensional models of structures, each standard model of each structure comprising a plurality of modes of deformation;
    generating a synthesized image of the structure using the standard model, the synthesized image having an associated projection angle;
    comparing a projection image of the object, taken at the associated projection angle, to the synthesized image to obtain a measurement of differences between the synthesized image and the projection image; and
    modifying the standard model of the structure to generate a customized model of the object by selectively varying at least one mode of deformation of the standard model and repeating the steps of generating, comparing and modifying until the measurement of differences is within a desired threshold.

6. The method of claim 1, wherein the density map comprises an M×N array of density value entries, and wherein generating a two-dimensional density map comprises:
    generating a synthesized projection image of the customized model at a projection angle associated with the projection image of the object, the projection image and the synthesized projection image each comprising an M×N array of pixels; and
    for each entry in the density map, storing a value associated with a relationship between a projection image pixel and a synthesized projection image pixel at similar locations in the respective synthesized projection image and the projection image.

7. The method of claim 6, wherein the mathematical relationship is:

$$G_{(M,N)} = DXA\_PI_{(M,N)}/DRR_{(M,N)},$$

wherein DXA_PI(M,N) is a first pixel intensity value of the projection image at location (M,N), and DRR(M,N) is a second pixel intensity value of the synthesized projection image at location (M,N).

8. A system for assessing characteristics of an object includes:
    a processor;
    a storage medium for storing a projection image of an object;
    program code stored in the storage medium and operable when executed upon by the processor to:
        generate a customized a model of the object using a generic model of the object and the projection image of the object, the customized model comprising at least one volume element, the at least one volume element including density information;
        generate a density map using a synthesized projection image of the customized model and a projection image of the object; and
        modify the density information of the at least one volume element with information from the density map into the customized model to provide a density enhanced customized model of the object and thereby transform the generic model of the object into an object specific model; and wherein the density enhanced customized model of the object is stored in the storage medium.

9. The system of claim 8, wherein the program code stored in the storage medium and operable when executed by the processor to modify the density information of the at least one volume element with information from the density map into the customized model comprises the program code stored in the storage medium and operable when executed by the processor to back-project gains from the density map into the customized model.

10. The system of claim 8, wherein the density map comprises an M×N array of density values and wherein the program code that is operable to generate a density map includes program code operable to:

generate a synthesized projection image of the customized model at a projection angle associated with the projection image of the object, the projection image and the synthesized projection image each comprising an M×N array of pixels; and for each (M,N) entry in the density map, store a value associated with a relationship between a first image pixel at an (M,N) location of the projection image and a second image pixel at an (M,N) location of the synthesized projection image pixel.

11. The system of claim 10, wherein the relationship is defined by the below equation:

$$G(M,N)=DXA\_PI(M,N)/DRR(M,N)$$

wherein $DXA\_PI(M,N)$ is a pixel intensity value of the projection image at location (M,N) and $DRR(M,N)$ is the pixel intensity value of the synthesized projection image at location (M,N).

* * * * *